(12) United States Patent
Uhm

(10) Patent No.: US 7,229,284 B2
(45) Date of Patent: Jun. 12, 2007

(54) DENTAL ARTICULATOR HAVING DUAL BALLS

(75) Inventor: Jae Soo Uhm, Seoul (KR)

(73) Assignee: Alphadent Co., Ltd., Paju-si (KR)

( * ) Notice: Subject to any disclaimer, the term of this patent is extended or adjusted under 35 U.S.C. 154(b) by 0 days.

(21) Appl. No.: 11/177,546

(22) Filed: Jul. 8, 2005

(65) Prior Publication Data
US 2006/0204921 A1   Sep. 14, 2006

(30) Foreign Application Priority Data
Mar. 12, 2005   (KR)   ...................... 10-2005-0020800

(51) Int. Cl.
*A61C 11/00* (2006.01)
(52) U.S. Cl. .............................. 433/64; 433/60; 433/62
(58) Field of Classification Search .................. 433/64, 433/62, 63, 65, 66, 67
See application file for complete search history.

(56) References Cited

U.S. PATENT DOCUMENTS 2,765,533 A * 10/1956 McMorris ..................... 433/60
3,019,529 A * 2/1962 Hinze ........................... 433/64
4,196,518 A * 4/1980 Benzaria ....................... 433/60
5,592,809 A * 1/1997 Marcotrigiano et al. ....... 59/25

* cited by examiner

*Primary Examiner*—Melba N. Bumgarner
*Assistant Examiner*—Jonathan Werner
(74) *Attorney, Agent, or Firm*—Clark & Elbing LLP

(57) ABSTRACT

A dental articulator capable of finely adjusting a three-dimensional articulation posture and exerting a secure fastening force by a lever is provided. The dental articulator includes a lower grip plate, a column, an arm, and an upper grip plate, wherein a first ball and a second ball are disposed between the arm and the upper grip plate, and wherein the dental articulator further comprises: a first clamp block having spherical recesses contacting with the first and second balls; a second clamp block having spherical recesses contacting with the first and second balls; a lever disposed on an outer surface of the second clamp block; an engaging bolt passing through the lever and the second clamp block into the first clamp block; and fastening bolts engaged into the lever to shorten a distance between the first and second clamp blocks.

3 Claims, 5 Drawing Sheets

DENTAL ARTICULATOR HAVING DUAL BALLS

CROSS-REFERENCE TO RELATED PATENT APPLICATION

This application claims the benefit of Korean Patent Application No. 10-2005-0020800, filed on Mar. 12, 2005, in the Korean Intellectual Property Office, the disclosure of which is incorporated herein in its entirety by reference.

BACKGROUND OF THE INVENTION

1. Field of the Invention

The present invention relates to a dental articulator, and more particularly, to a dental articulator capable of accurately adjusting a three-dimensional articulation posture.

2. Description of the Related Art

In general, a dental articulator is a tool for producing artificial teeth, or dentures. An orthodontist mounts teeth molds made by a dentist on the dental articulator to produce the artificial teeth.

One type of conventional dental articulators comprises a base, a column erected at one end of the base, and arm rotatably disposed at one end of the column. Plaster molds are mounted on the base and attached to the arm. After the plaster molds are solidified, the plaster molds are hit and detached from the dental articulator. Due to hitting, the plaster molds may be damaged or broken. In addition, wastes of the plaster molds may contaminate environments. In addition, it takes too much time to solidify the plaster molds.

Another type of conventional dental articulators further comprises fastening means including upper and lower grippers for gripping upper and lower mouth molds on the arm and base. The upper and lower grippers are controlled with respective fastening bolts. In the conventional dental articulator, the grippers are fastened with engagement means. Therefore, after the articulation processes are performed several times, an engagement force is weaken, so that there may occur imperfect articulation due to change in an articulation posture of the dental articulator.

SUMMARY OF THE INVENTION

The present invention provides a dental articulator capable of finely adjusting a three-dimensional articulation posture and exerting a secure fastening force by means of a lever.

According to an aspect of the present invention, there is provided a dental articulator comprising: a lower grip plate on which a lower mouth mold is mounted; a column disposed at one end of the lower grip plate; an arm having one end rotatably disposed at upper end of the column; and an upper grip plate disposed at the other end of the arm, wherein a first ball having a shape of sphere is disposed at the other end of the arm, and a second ball having a shape of sphere is disposed at a neck portion erected at a center of the upper grip plate, and wherein the dental articulator further comprises: a first clamp block having spherical recesses spherically contacting with the first and second balls, wherein a screw hole is provided at a central portion of the first clamp block; a second clamp block having spherical recesses spherically contacting with the first and second balls, wherein an engaging bolt hole is provided at a central portion of the second clamp block; and an engaging bolt passing through the engaging bolt hole of the second clamp block to be engaged into the screw hole of the first clamp block.

In the aspect of the present invention, the dental articulator may further comprise: a lever disposed on an outer surface of the second clamp block, wherein screw holes are provided to both ends of the lever, wherein an engaging bolt hole is provided to a central portion of the lever; and fastening bolts engaged into the screw holes of the lever to shorten a distance between the first and second clamp blocks based on the engagement position.

In the aspect of the present invention, the lever may be inserted into a groove formed on the outer surface of the second clamp block to prevent the lever from rotating.

In addition, the engaging bolt may be located at a central portion between the first and second balls, and central axes of the fastening bolts may be located close to the central lines of the respective first and second balls.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Now, preferred embodiments of the present invention will be described with reference to the accompanying drawings.

Figure 1:
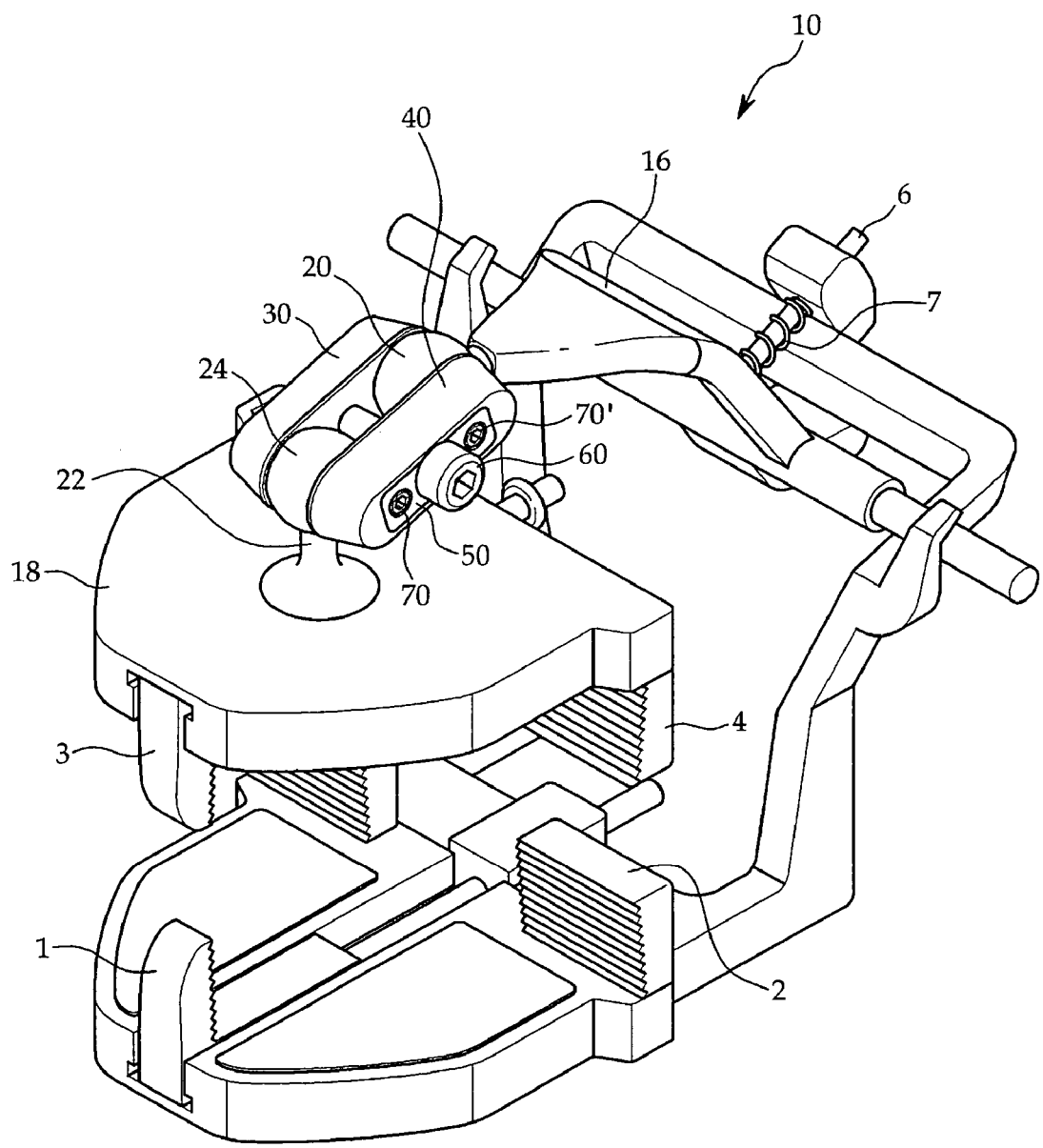
FIG. 1 is a perspective view showing a dental articulator according to the present invention.
Figure 2:
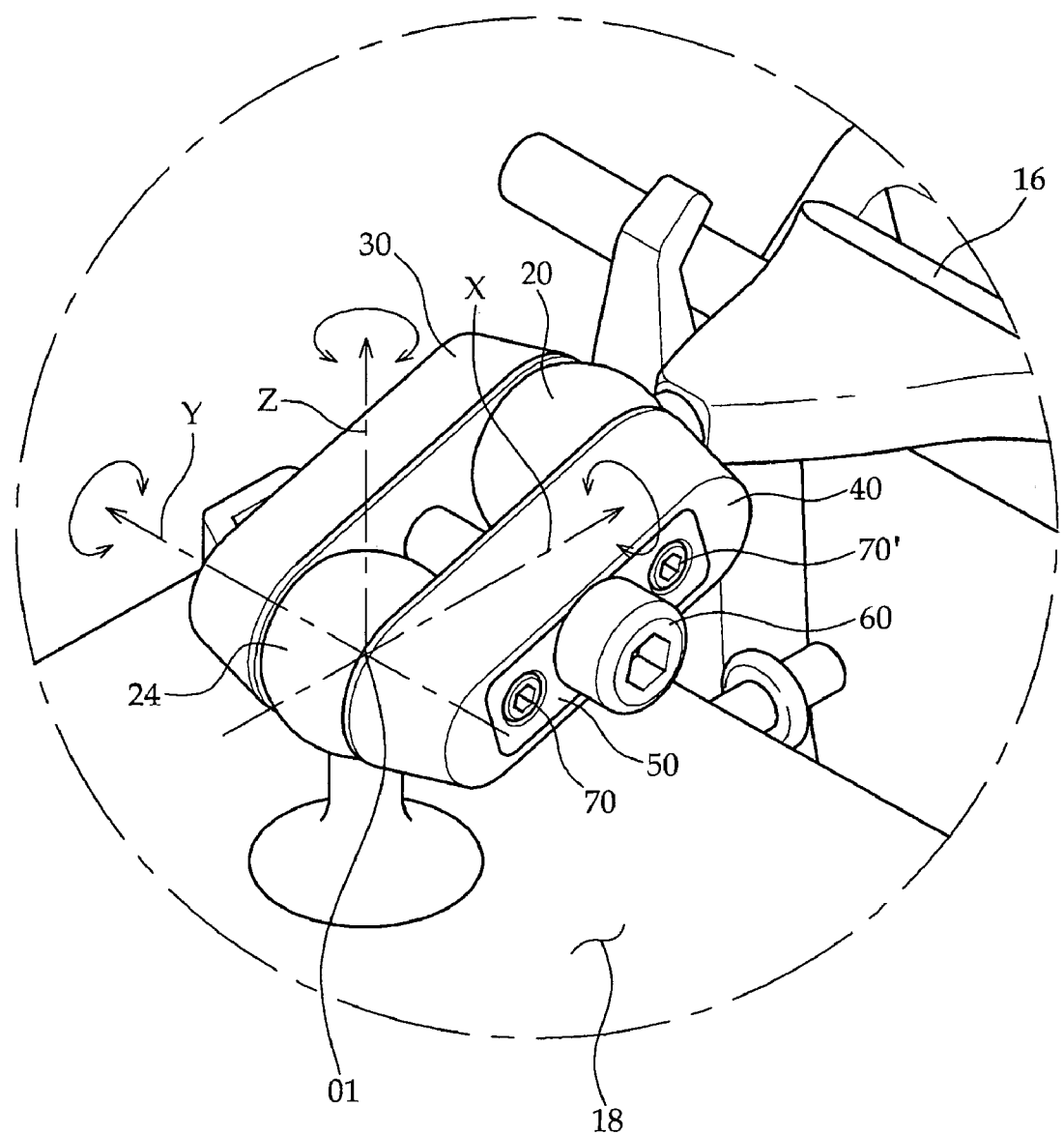
FIG. 2 is an enlarged view showing a principal portion of the dental articulator of FIG. 1.
Figure 3:
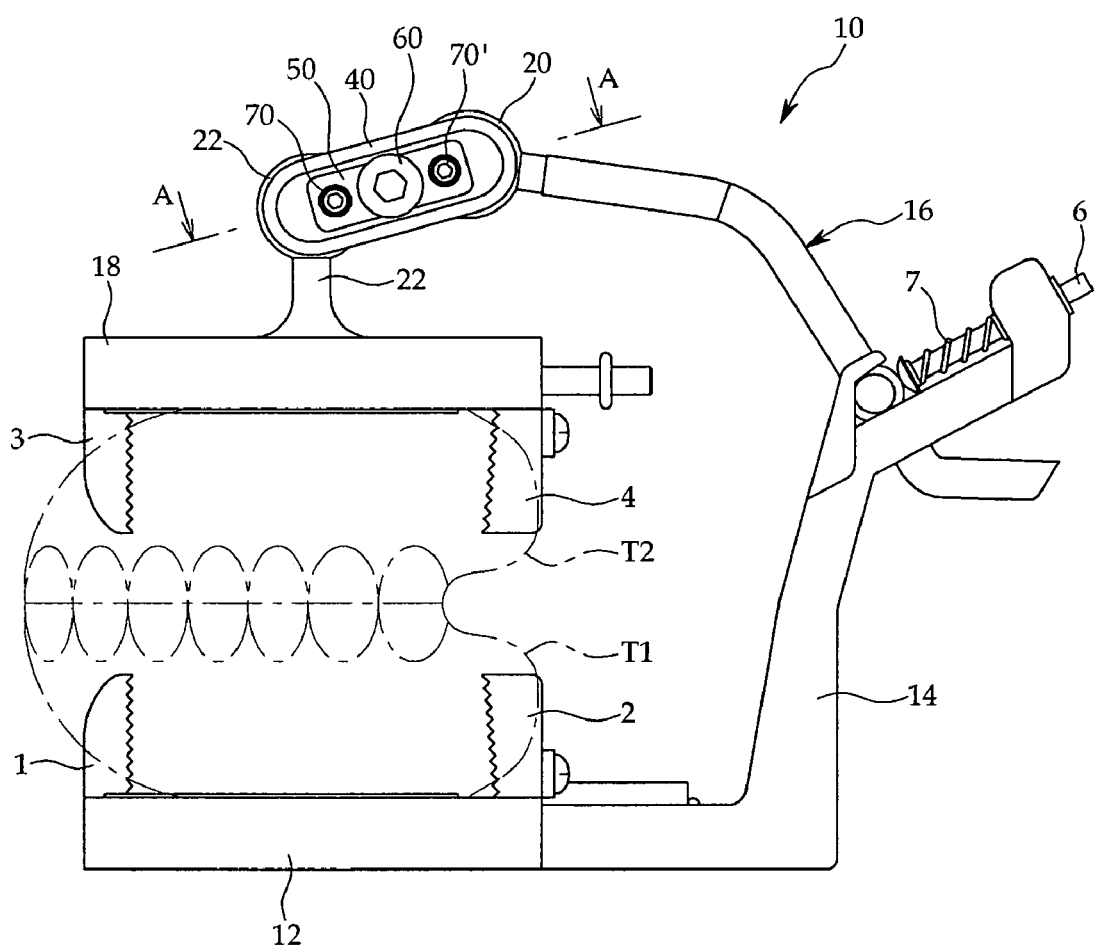
FIG. 3 is a plan view showing the dental articulator of FIG. 1.
Figure 4:
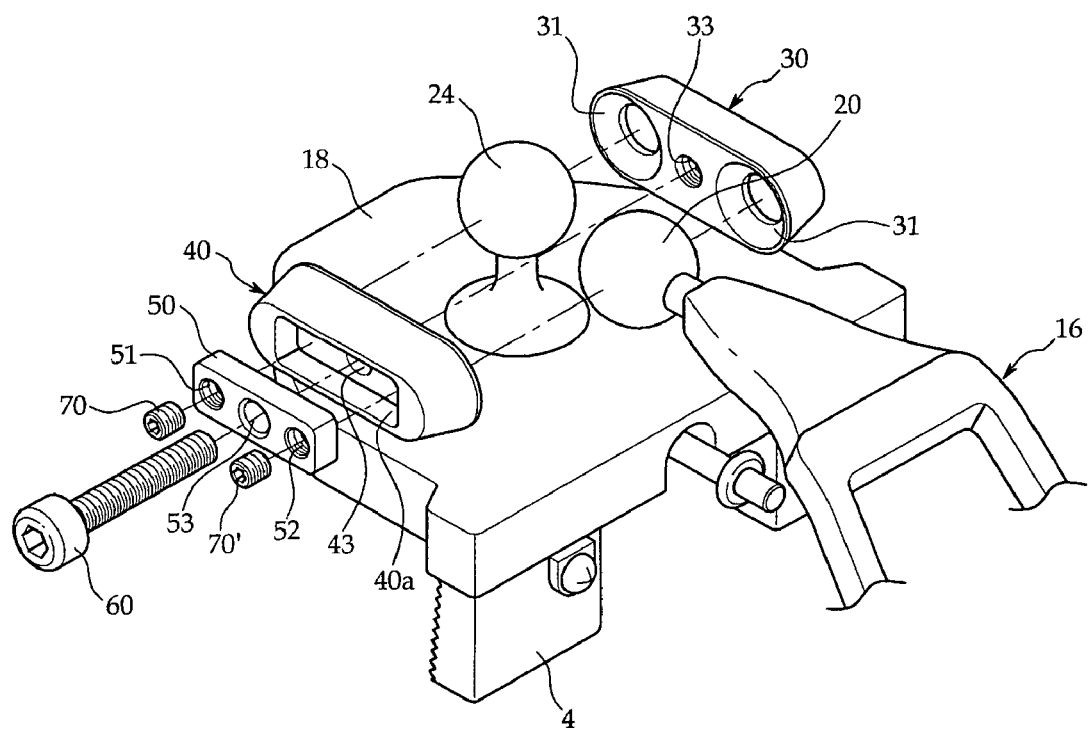
FIG. 4 is a perspective exploded view showing a principal portion of the dental articulator of FIG. 2.
Figure 5:
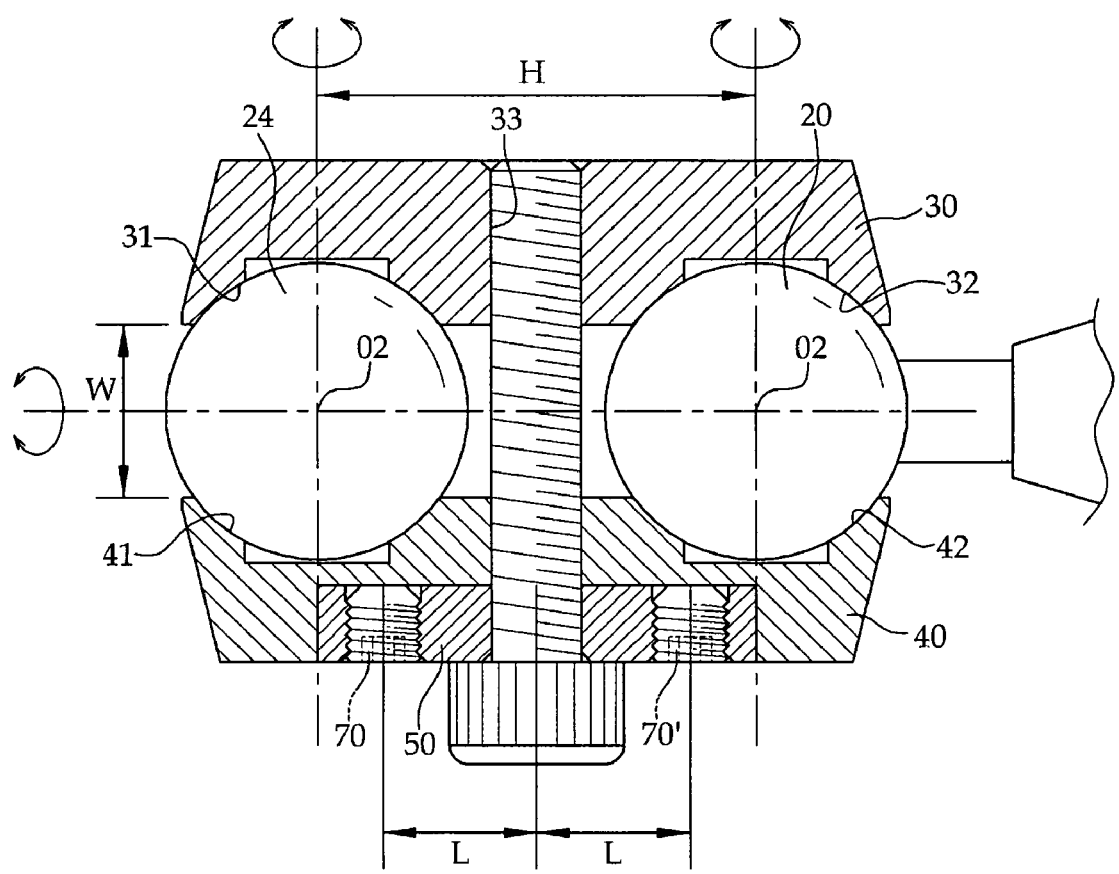
FIG. 5 is a cross sectional view taken along a line A—A of FIG. 3.

FIG. 1 is a perspective view showing a dental articulator 10 according to the present invention. FIG. 2 is an enlarged view showing a principal portion of the dental articulator of FIG. 1. FIG. 3 is a plan view showing the dental articulator of FIG. 1. FIG. 4 is a perspective exploded view showing a principal portion of the dental articulator of FIG. 2. FIG. 5 is a cross sectional view taken along a line A—A of FIG. 3.

As shown in FIGS. 1 to 3, the dental articulator 10 according to the present invention includes a lower grip plate 12 on which a lower mouth mold T1 is mounted, a column 14 disposed at one end of the lower grip plate 12, an arm 16 having one end rotatably disposed at the column 14, and an upper grip plate 18 disposed at the other end of the arm 16. An upper mouth mold T2 is mounted on the upper grip plate 18. In addition, the one end of the arm 16 may be detachable from the column 14.

In addition, grippers 1 and 2 for gripping the mouth mold T1, one of which is movable in opposite direction, are disposed on the lower grip plate 12. Further, grippers 3 and 4 for gripping the mouth mold T2, one of which is movable in opposite direction, are disposed on the upper grip plate 18. Since structures and operations of the grippers 1, 2, 3, and 4 are well known to the ordinarily skilled, description on the gripper 1, 2, 3, and 4 will be omitted.

According to the present invention, a first ball 20 having a shape of sphere is disposed at the other end of the arm 16.

In addition, a second ball 24 having a shape of sphere is disposed at a neck portion 22. The neck portion 22 is erected at a center of the upper grip plate 18. In the embodiment, the first and second balls 20 and 24 may have the same size.

First and second clamp blocks 30 and 40 are provided to spherically contact with the first and second balls 20 and 24.

More specifically, referring to FIGS. 4 and 5, spherical recesses 31 and 32 are provided in an inner surface of the first clamp block 30 to contact with the first and second balls 20 and 24. In addition, a screw hole 33 is provided at a central portion of the first clamp block 30.

On the other hand, referring to FIGS. 4 and 5, spherical recesses 41 and 42 are provided in an inner surface of the second clamp block 40 to contact with the first and second balls 20 and 24. In addition, an engaging bolt hole 43 is provided at a central portion of the second clamp block 40.

A distance between centers O1 and O2 of the spherical recesses 31 and 32 of the first clamp block 30 is equal to a distance between centers O1 and O2 of the spherical recesses 41 and 42 of the second clamp block 40. Therefore, the screw hole 33 and engaging bolt hole 43 are disposed along a straight line.

A lever 50 is disposed on an outer surface of the second clamp block 40. Screw holes 51 an 52 are provided to both ends of the lever 50, and an engaging bolt hole 53 is provided to a central portion of the lever 50.

Preferably, in order to prevent the lever 50 from rotating, the lever 50 is inserted into a groove 40a formed on the outer surface of the second clamp block 40. More specifically, the lever 50 has a shape of an approximately rectangle, so that the lever 50 inserted into the groove cannot move. Therefore, when an engaging bolt 60 described later is preliminarily engaged, the lever 50 cannot move.

The engaging bolt 60 passes through the engaging bolt hole 53 of the lever 50 and the engaging bolt hole 43 of the second clamp block 40 to be engaged into the screw hole 33 of the first clamp block 30.

The engaging bolt 60 preliminarily engages the first and second clamp blocks 30 and 40 between which the first and second balls 20 and 24 are interposed.

Fastening bolts 70 and 70' are engaged into the screw holes 51 and 52 of the lever 50. By fastening the fastening bolts 70 and 70', the distance W between the first and second clamp blocks 30 and 40 is shortened to fasten the first and second balls 20 and 24.

In the figures, reference numerals 6 and 7 indicate a pusher and a compression spring, respectively. When the pusher 6 is pushed, the compression spring 7 and the pusher 6 exert a force on the arm 16, so that the arm 16 can rotate in a predetermined direction.

Now, operations of the dental articulator according to the present invention will be described.

(Preliminary Engagement of Clamp Blocks)

Firstly, as shown in FIG. 4, the first ball 20 connected to the arm 16 is brought close to the second ball 24 disposed on the upper grip plate 18. Next, the first and second clamp blocks 30 and 40 are preliminarily engaged with the engaging bolt 60. As a result, the spherical recesses 31 and 32 of the first clamp block 30 and the spherical recesses 41 and 42 of the second clamp block 40 spherically contact with the first and second balls 20 and 24.

The preliminary engagement is a weak engagement of the engaging bolt 60. Therefore, the upper grip plate 10 can freely change its three-dimensional posture with reference to the center O1 of the first ball 20 or the center O2 of the second ball 24.

More specifically, the upper grip plate 10 can freely change its three-dimensional posture due to a spherical sliding contact of the first and second balls 20 and 24 with the spherical recesses 31, 32 and 41, 42. In addition, due to the distance H between the first and second balls 20 and 24, a height of the upper grip plate 10 can change.

The upper grip plate 18 can rotate about the three axes (X, Y, and Z axes) with respect to each of the centers O1 and O2 of the first and second balls 20 and 24. The upper grip plate 18 can have any movements: horizontal rotation; left and right tilts; foreword and backward movements; leftward and rightward movement; and upward and downward movements. The upwards and downward movements means a change in the height of the upper grip plate 18. Since the upper grip plate 10 can freely change its three-dimensional posture, it is possible to accurately articulate the upper and lower mouth molds T1 and T2.

(Fixing Posture with Grippers)

After the posture of the upper grip plate 18 is set up by using the engaging bolt 60, a fastening force is exerted by using the fastening bolts 70 and 70' engaged in to the screw holes 51 and 52 of the lever 50.

Namely, if the fastening bolts 70 and 70' are screwed, the first clamp block 30 is pulled by means of the lever 50, and the second clamp block 40 is pushed. Therefore, the first and second clamp blocks 30 and 40 pull each other, so that a strong fastening force is exerted between the first and second clamp blocks 30 and 40 and the first and second balls 20 and 24.

The lever 50 is fastened to the first clamp block 30 through the engaging bolt 60 by the fastening force. The associated moment is exerted between the fastening bolt 70 and the engaging bolt 60 separated from each other by a distance L.

The upper grip plate 18 is securely fastened by using the lever, so that it is possible to increase the fastening force in comparison to a conventional fastening mechanism using such a plaster material.

In addition, since the posture of the upper grip plate 18 is accurately set up by using a spherical contact during the preliminary engagement of the engaging bolt 60, it is possible to accurately articulate the upper and lower mouth molds.

According to the present invention, a dental articulator has dual balls ratable around two axes, and the posture of the dental articulator can be three-dimensionally set up, so that it is possible to accurately articulate an upper grip plate. In addition, is possible to improve reliability of articulation by using a strong fastening force by means of a lever.

While the present invention has been particularly shown and described with reference to exemplary embodiments thereof, it will be understood by those skilled in the art that various changes in form and details may be made therein without departing from the spirit and scope of the present invention as defined by the appended claims.

What is claimed is:

1. A dental articulator comprising:
   a lower grip plate on which a lower mouth mold is mounted;
   a column disposed at one end of the lower grip plate;
   an arm having one end rotatably disposed at an upper end of the column; and
   an upper grip plate disposed at the other end of the arm, wherein a first ball having a shape of a sphere is disposed at the other end of the arm, and a second ball having a shape of a sphere is disposed at a neck portion erected at a center of the upper grip plate, and wherein the dental articulator further comprises:
a first clamp block having spherical recesses spherically contacting with the first and second balls, wherein a screw hole is provided at a central portion of the first clamp block;
a second clamp block having spherical recesses spherically contacting with the first and second balls, wherein an engaging bolt hole is provided at a central portion of the second clamp block;
a lever disposed on an outer surface of the second clamp block, wherein screw holes are provided to both ends of the lever, wherein an engaging bolt hole is provided to a central portion of the lever;
an engaging bolt passing through the engaging bolt hole of the lever and the engaging bolt hole of the second clamp block to be engaged into the screw hole of the first clamp block; and
fastening bolts engaged into the screw holes of the lever to shorten a distance between the first and second clamp blocks based on the fastening bolts' engagement position.

2. The dental articulator according to claim 1, wherein the lever is inserted into a groove formed on the outer surface of the second clamp block to prevent the lever from rotating.

3. The dental articulator according to claim 1, wherein the engaging bolt is located at a central portion between the first and second balls, and wherein central axes of the fastening bolts are located close to central lines of the respective first and second balls.

* * * * *